US009884007B2

(12) United States Patent
Constantine et al.

(10) Patent No.: US 9,884,007 B2
(45) Date of Patent: Feb. 6, 2018

(54) COMPOSITION

(71) Applicant: Cosmetic Warriors Limited, Poole, Dorset (GB)

(72) Inventors: Mark Constantine, Poole (GB); Margaret Joan Constantine, Poole (GB); Helen Elizabeth Ambrosen, Wimborne (GB)

(73) Assignee: COSMETIC WARRIORS LIMITED, Poole, Dorset (GB)

( * ) Notice: Subject to any disclaimer, the term of this patent is extended or adjusted under 35 U.S.C. 154(b) by 181 days.

(21) Appl. No.: 14/411,755

(22) PCT Filed: Jun. 27, 2013

(86) PCT No.: PCT/GB2013/051700
§ 371 (c)(1),
(2) Date: Dec. 29, 2014

(87) PCT Pub. No.: WO2014/001806
PCT Pub. Date: Jan. 3, 2014

(65) Prior Publication Data
US 2015/0157554 A1 Jun. 11, 2015

(30) Foreign Application Priority Data
Jun. 29, 2012 (GB) .................................. 1211531.7

(51) Int. Cl.
| A61K 8/97 | (2017.01) |
| A61K 8/60 | (2006.01) |
| A61Q 19/10 | (2006.01) |
| C11D 9/26 | (2006.01) |
| C11D 9/38 | (2006.01) |
| C11D 13/26 | (2006.01) |
| A61K 8/36 | (2006.01) |
| A61K 8/02 | (2006.01) |
| A45D 40/00 | (2006.01) |

(52) U.S. Cl.
CPC .............. *A61K 8/97* (2013.01); *A61K 8/0216* (2013.01); *A61K 8/361* (2013.01); *A61K 8/60* (2013.01); *A61Q 19/10* (2013.01); *C11D 9/262* (2013.01); *C11D 9/38* (2013.01); *C11D 13/26* (2013.01); *A45D 40/00* (2013.01); *A61K 2800/42* (2013.01); *A61K 2800/48* (2013.01)

(58) Field of Classification Search
None
See application file for complete search history.

(56) References Cited

U.S. PATENT DOCUMENTS

| 5,994,281 A * | 11/1999 | He | C11D 17/006 |
| | | | 510/141 |
| 2004/0022818 A1 | 2/2004 | Cho et al. | |
| 2006/0052263 A1 | 3/2006 | Roreger et al. | |
| 2006/0134045 A1 | 6/2006 | Cao et al. | |
| 2008/0095807 A1 | 4/2008 | Zabari | |
| 2008/0242572 A1 | 10/2008 | Icht et al. | |
| 2012/0082657 A1 | 4/2012 | Yim | |

FOREIGN PATENT DOCUMENTS

| CN | 1730643 | 2/2006 |
| CN | 102041205 A | 5/2011 |
| CN | 102563642 | 7/2012 |
| EP | 0357496 B1 | 5/1994 |
| EP | 1992322 A1 | 11/2008 |
| EP | 2604678 A1 | 6/2013 |
| JP | S52-051033 A | 4/1977 |
| JP | H08-06019 A | 3/1996 |
| JP | 9-87687 A | 3/1997 |
| JP | 2000-273495 A | 10/2000 |
| JP | 2001-031560 A | 2/2001 |
| JP | 2003-138295 A | 5/2003 |
| JP | 2005-82685 A | 3/2005 |
| JP | 2005-538202 A | 12/2005 |
| JP | 2005-538982 A | 12/2005 |
| JP | 2007-022931 A | 2/2007 |
| JP | 2007-297335 A | 11/2007 |
| JP | 2008-297215 A | 12/2008 |
| JP | 2009-149599 A | 7/2009 |
| JP | 2010-46129 A | 3/2010 |
| JP | 2011-052168 | 3/2011 |
| JP | 2011-190188 A | 9/2011 |
| JP | 2012-41376 A | 3/2012 |
| RU | 2343900 C2 | 1/2009 |

(Continued)

OTHER PUBLICATIONS

Beijing Ruiya Culture Communication Co Ltd: "Fruit Soap"; Beauty Body with Small Money, China Light Industry Pres, China, Aug. 31, 2005, pp. 93-94.
International Search report and Written Opinion for International Application No. PCT/GB2013/051700 mailed May 14, 2014 (21 pages).
Database GNPD Mintel: "Pink Grapefruit & Melon Glycerine Soap." Mar. 2012.
Database GNPD Mintel: "Scents from Brazil Soap Kit." Apr. 2010.
Wei Zhao, "Diet code for anti-cancer", China Textile Press (2004), pp. 218-219.
Li Jielian et al., "Hypertension Self Health Management Book", Tianjin Science and Technology Press (2009), pp. 166.
Office Action for Chinese Patent Application No. 201380034707.8, dated Mar. 6, 2017.

(Continued)

Primary Examiner — Necholus Ogden, Jr.

(74) Attorney, Agent, or Firm — Merchant & Gould P.C.

(57) ABSTRACT

A solid cosmetic composition includes (i) sugar; (ii) a vegetable fiber, a fruit fiber or mixture thereof; and (iii) a soap. The solid cosmetic composition is prepared by dehydrating a liquid composition including (i) sugar in an amount of 33.75 to 47 wt. %; (ii) a vegetable fiber, a fruit fiber or mixture thereof, in an amount of 3.75 to 4.75 wt. %; (iii) a soap in an amount of 20 to 75 wt. %; and (iv) water in an amount of 11 to 15 wt. %. The amounts are based on the total combined amount of the sugar, the fiber, the soap and the water.

24 Claims, No Drawings

(56) References Cited

FOREIGN PATENT DOCUMENTS

WO    2004/008887 A1    1/2004
WO    WO 2007/142221    12/2007
WO    2009/022615 A1    2/2009

OTHER PUBLICATIONS

Office Action for Japanese Patent Application No. 2015-519344, dated Mar. 28, 2017.
Nuannuan: Natural exfoliating retinervus luffae fructus handmade Soap, hftp://blog.sina.com.cn/celiacn, pp. 1-7 (2011).
Office Action for Chinese Patent Application No. 201380034707.8, dated Aug. 24, 2016.
Decision to Grant for Russian Patent Application No. 2015102572/15(003991), dated Mar. 23, 2017.
Search Report for Japanese Patent Application No. 20015-519344, dated Mar. 27, 2017.

\* cited by examiner

COMPOSITION

This application is a National Stage Application of PCT/GB2013/051700, filed 27 Jun. 2013, which claims benefit of Serial No. 1211531.7, filed 29 Jun. 2012 in Great Britain and which applications are incorporated herein by reference. To the extent appropriate, a claim of priority is made to each of the above disclosed applications.

FIELD OF THE INVENTION

The present invention relates to a solid product for use as a cosmetic, a process for producing said product, and a product prepared by the method.

BACKGROUND TO THE INVENTION

The present invention relates to products particularly those for use in contact with the human body.

The history of soap and its use in cosmetics dates back many hundreds of years. It has therefore a very long history of safe use. The properties of soap and its manufacture make it very interesting from an environmental perspective. Soaps are salts of fatty acids and can be made from a number of fatty sources. Traditionally soap was made from tallow. Over the last few decades it has been made from vegetable oils in response to a demand for non-animal based products. Soap is a relatively simple material and it can be manufactured locally by cosmetic manufacturers, unlike synthetic detergents whose manufacture is far more complicated and beyond normal manufacturing capabilities. Soap is an alkaline medium. As such it does not require cosmetic preservatives. It is a solid medium so it does not require packaging to contain it. All these considerations make it an exceptional material and its versatility is extremely useful.

Soap and surfactants have been provided in many physical forms. One form previously provided has been as 'paper' type sheet. For example cellulose derivatives can be combined with surfactants to form a paper like product. These paper type products have been typically either fragile flakeable materials or thick sheets. However, owing to the constraints of the ingredient materials, 'paper' type products which are foldable and pliable have not been prepared.

The present invention seeks to provide a solid cosmetic product which is foldable without snapping and which can be used in the manner of paper, for example as a wrapping material, as well as being a soap product that can be washed with.

SUMMARY OF THE INVENTION

In a first aspect, there is provided a solid cosmetic composition comprising
(i) sugar;
(ii) a vegetable fibre, a fruit fibre or mixture thereof; and
(iii) a soap;
wherein the solid cosmetic composition is prepared by dehydrating a liquid composition comprising
(i) sugar in an amount of 33.75 to 47 wt. %;
(ii) a vegetable fibre, a fruit fibre or mixture thereof, in an amount of 3.75 to 4.75 wt. %;
(iii) a soap in an amount of 20 to 75 wt. %; and
(iv) water in an amount of 11 to 15 wt. %,
wherein the amounts are based on the total combined amount of the sugar, the fibre, the soap and the water.

In a second aspect, there is provided a solid cosmetic composition comprising
(i) sugar;
(ii) melon fibre; and
(iii) a soap,
wherein the solid cosmetic composition is prepared by dehydrating a liquid composition comprising
(a) melon; and
(b) a soap.

In a third aspect, there is provided a solid cosmetic composition comprising
(i) sugar;
(ii) a vegetable fibre, a fruit fibre or mixture thereof; and
(iii) a soap;
wherein the solid cosmetic composition is prepared by dehydrating a liquid composition comprising
(i) sugar in an amount of 6.75 to 8.6 wt. %;
(ii) a vegetable fibre, a fruit fibre or mixture thereof, in an amount of 0.75 to 0.95 wt. %;
(iii) a soap in an amount of 5 to 25 wt. %; and
(iv) water in an amount of 67.5 to 85.5 wt. %,
wherein the amounts are based on the total combined amount of the sugar, the fibre, the soap and the water.

In a fourth aspect, there is provided a process for preparing a solid cosmetic composition comprising
(i) sugar;
(ii) a vegetable fibre, a fruit fibre or mixture thereof; and
(iii) a soap;
the process comprising the step of
(a) providing a liquid composition comprising
(i) sugar in an amount of 6.75 to 8.6 wt. %;
(ii) a vegetable fibre, a fruit fibre or mixture thereof, in an amount of 0.75 to 0.95 wt. %;
(iii) a soap in an amount of 5 to 25 wt. %; and
(iv) water in an amount of 67.5 to 85.5 wt. %,
wherein the amounts are based on the total combined amount of the sugar, the fibre, the soap and the water,
(b) dehydrating the liquid composition to provide the solid cosmetic composition.

In a fifth aspect, there is provided a product obtained or obtainable by a process in accordance with the present invention.

For ease of reference, these and further aspects of the present invention are now discussed under appropriate section headings. However, the teachings under each section are not necessarily limited to each particular section.

ADVANTAGES

We have surprisingly found that by providing a solid cosmetic composition comprising the specific components of the present invention as described herein, a soap is formed having physical characteristics which give a paper like texture. The present invention provides a solid cosmetic composition which may be used in the form of packaging, which can be used to wrap other products. This wrapping material can be used to protect them, for example in a retail environment. It is also possible to print information on to the compositions of the present invention, so we have surprisingly found that we may provide a wrapping, which for example explains the contents of the product within. When the wrapping made from the composition of the present invention has been removed, it can subsequently be used to wash the skin. This is highly advantageous because the packaging is used for a further purpose and does not create any solid waste, for example which has to be collected for recycling or which would end up in land fill. This is an exceptional aspect as the creation of excessive packaging is environmentally challenging.

The present invention provides a form of paper prepared from soap (with the addition of water), fibre and sugar. This forms an excellent paper like texture. It has been surprisingly found that a blend of these ingredients when dehydrated formed a durable material which has the desired properties.

DETAILED DESCRIPTION

Composition

As discussed herein, the present invention provides a solid cosmetic composition comprising (i) sugar; (ii) a vegetable fibre, a fruit fibre or mixture thereof; and (iii) a soap; wherein the solid cosmetic composition is prepared by dehydrating a liquid composition comprising (i) sugar in an amount of 33.75 to 47 wt. %; (ii) a vegetable fibre, a fruit fibre or mixture thereof, in an amount of 3.75 to 4.75 wt. %; (iii) a soap in an amount of 20 to 75 wt. %; and (iv) water in an amount of 11 to 15 wt. %, wherein the amounts are based on the total combined amount of the sugar, the fibre, the soap and the water a solid cosmetic composition comprising (i) sugar; (ii) a vegetable fibre, a fruit fibre or mixture thereof; and (iii) a soap; wherein the solid cosmetic composition is prepared by dehydrating a liquid composition comprising (i) sugar in an amount of 6.75 to 8.6 wt. %; (ii) a vegetable fibre, a fruit fibre or mixture thereof, in an amount of 0.75 to 0.95 wt. %; (iii) a soap in an amount of 5 to 25 wt. %; and (iv) water in an amount of 67.5 to 85.5 wt. %, wherein the amounts are based on the total combined amount of the sugar, the fibre, the soap and the water.

a solid cosmetic composition comprising (i) sugar; (ii) melon fibre; and (iii) a soap, wherein the solid cosmetic composition is prepared by dehydrating a liquid composition comprising (a) melon; and (b) a soap.

It will be understood by one skilled in the art that a soap is a salt of fatty acid.

The solid products of the present invention are compositions which can substantially sustain their physical shape when unsupported by external means, e.g. packaging etc. Thus, they are considered to be solid, solid like, in solid form or in solid-like form at room temperature. For the avoidance of doubt the solid product must remain substantially solid at up to 30° C.

By solid-like, it is understood that some materials are considered on a day to day basis to be solid, yet over an extremely long period of time, may alter in shape, e.g. amorphous materials such as glass etc. However, they are considered to be solid-like as, for the purpose they fulfil, they are solid.

Due to the solid form of the compositions of the present invention, external packaging is not required to maintain the shape of the composition.

The composition of the present invention is typically provided in the form of a sheet. As will be understood by one skilled in the art, by sheet it is meant a product having thickness of less than 5 mm, such as less than 4 mm, such as less than 2 mm, such as 1 to 2 mm.

Sugar

The surfactant product of the present invention comprises sugar. A sugar as described herein is a mono-saccharide or a disaccharide. Thus references herein to sugar may be read to mean mono-saccharides, disaccharides or mixtures thereof. In one aspect the sugar is selected from mono-saccharides. In one aspect the sugar is selected from disaccharides.

In one aspect the present invention provides a solid cosmetic composition comprising (i) one or more di-saccharides; (ii) a vegetable fibre, a fruit fibre or mixture thereof; and (iii) a soap; wherein the solid cosmetic composition is prepared by dehydrating a liquid composition comprising (i) one or more di-saccharides in an amount of 33.75 to 47 wt. %; (ii) a vegetable fibre, a fruit fibre or mixture thereof, in an amount of 3.75 to 4.75 wt. %; (iii) a soap in an amount of 20 to 75 wt. %; and (iv) water in an amount of 11 to 15 wt. %, wherein the amounts are based on the total combined amount of the one or more di-saccharides, the fibre, the soap and the water. In one aspect the present invention provides a solid cosmetic composition comprising (i) sucrose; (ii) a vegetable fibre, a fruit fibre or mixture thereof; and (iii) a soap; wherein the solid cosmetic composition is prepared by dehydrating a liquid composition comprising (i) sucrose in an amount of 33.75 to 47 wt. %; (ii) a vegetable fibre, a fruit fibre or mixture thereof, in an amount of 3.75 to 4.75 wt. %; (iii) a soap in an amount of 20 to 75 wt. %; and (iv) water in an amount of 11 to 15 wt. %, wherein the amounts are based on the total combined amount of the sucrose, the fibre, the soap and the water.

In one aspect the present invention provides a solid cosmetic composition comprising (i) one or more di-saccharides; (ii) a vegetable fibre, a fruit fibre or mixture thereof; and (iii) a soap; wherein the solid cosmetic composition is prepared by dehydrating a liquid composition comprising (i) one or more di-saccharides in a combined amount of 6.75 to 8.6 wt. %; (ii) a vegetable fibre, a fruit fibre or mixture thereof, in an amount of 0.75 to 0.95 wt. %; (iii) a soap in an amount of 5 to 25 wt. %; and (iv) water in an amount of 67.5 to 85.5 wt. %, wherein the amounts are based on the total combined amount of the di-saccharides, the fibre, the soap and the water. In one aspect the sugar is sucrose. In one aspect the present invention provides a solid cosmetic composition comprising (i) sucrose; (ii) a vegetable fibre, a fruit fibre or mixture thereof; and (iii) a soap; wherein the solid cosmetic composition is prepared by dehydrating a liquid composition comprising (i) sucrose in an amount of 6.75 to 8.6 wt. %; (ii) a vegetable fibre, a fruit fibre or mixture thereof, in an amount of 0.75 to 0.95 wt. %; (iii) a soap in an amount of 5 to 25 wt. %; and (iv) water in an amount of 67.5 to 85.5 wt. %, wherein the amounts are based on the total combined amount of the sucrose, the fibre, the soap and the water.

In the product of the first aspect of the present invention, the sugar is present in an amount of 33.75 to 47 wt. % based on the total combined amount of the sugar, the fibre, the soap and the water. In one aspect the liquid composition comprises sugar in an amount of 35 to 46.5 wt. % based on the total combined amount of the sugar, the fibre, the soap and the water, such as in an amount of 36.5 to 46.5 wt. % based on the total combined amount of the sugar, the fibre, the soap and the water, such as in an amount of 38 to 45 wt. % based on the total combined amount of the sugar, the fibre, the soap and the water, such as in an amount of 39 to 42 wt. % based on the total combined amount of the sugar, the fibre, the soap and the water, such as in an amount of approximately 40.5 wt. % based on the total combined amount of the sugar, the fibre, the soap and the water. In the product of the first aspect of the present invention, the sucrose is present in an amount of 33.75 to 47 wt. % based on the total combined amount of the sucrose, the fibre, the soap and the water. In one aspect the liquid composition comprises sucrose in an amount of 35 to 46.5 wt. % based on the total combined amount of the sucrose, the fibre, the soap and the water, such as in an amount of 36.5 to 46.5 wt. % based on the total combined amount of the sucrose, the fibre, the soap and the water, such as in an amount of 38 to 45 wt. % based on the total combined amount of the sucrose, the fibre, the soap and the water, such as in an amount of 39 to 42 wt. % based on the total combined amount of the sucrose, the fibre, the soap and the water, such as in an amount of approximately 40.5 wt. % based on the total combined amount of the sucrose, the fibre, the soap and the water.

In the product to be dehydrated, the sugar is present in an amount of 6.75 to 8.6 wt. % based on the total combined amount of the sugar, the fibre, the soap and the water. In one aspect the solid cosmetic composition is preferably prepared by dehydrating a liquid composition comprising sugar in an amount of 7.1 to 8.6 wt. % based on the total combined amount of the sugar, the fibre, the soap and the water such as in an amount of 7.6 to 8.6 wt. % based on the total combined amount of the sugar, the fibre, the soap and the water, such as in an amount of 7.8 to 8.4 wt. % based on the total combined amount of the sugar, the fibre, the soap and the water, such as in an amount of 7.9 to 8.3 wt. % based on the total combined amount of the sugar, the fibre, the soap and the water, such as in an amount of approximately 8.1 wt. % based on the total combined amount of the sugar, the fibre, the soap and the water, such as in an amount of 7.1 to 8.1 wt. % based on the total combined amount of the sugar, the fibre, the soap and the water, such as in an amount of 7.4 to 7.9 wt. % based on the total combined amount of the sugar, the fibre, the soap and the water, such as in an amount of approximately 7.65 wt. % based on the total combined amount of the sugar, the fibre, the soap and the water. In one aspect the solid cosmetic composition is preferably prepared by dehydrating a liquid composition comprising sucrose in an amount of 7.1 to 8.1 wt. % based on the total combined amount of the sucrose, the fibre, the soap and the water, such as in an amount of 7.4 to 7.9 wt. % based on the total combined amount of the sucrose, the fibre, the soap and the water, such as in an amount of approximately 7.65 wt. % based on the total combined amount of the sucrose, the fibre, the soap and the water.

Fibre

The solid cosmetic product of the present invention comprises a vegetable fibre, a fruit fibre or mixture thereof. It will be understood by one skilled in the art that by the terms vegetable fibre and fruit fibre it is meant dietary fibre obtained from a vegetable or a fruit, such as a berry. The dietary fibre will typically be an insoluble dietary fibre. In one aspect the present invention comprises a vegetable fibre. In one aspect the present invention comprises a fruit fibre. In one aspect the present invention comprises a vegetable fibre and a fruit fibre.

In the product of the first aspect of the present invention, the solid cosmetic composition comprises a vegetable fibre, a fruit fibre or mixture thereof, in an amount of 3.75 to 4.75 wt. % based on the total combined amount of the sugar, the fibre, the soap and the water, such as in an amount of 4 to 4.75 wt. % based on the total combined amount of the sugar, the fibre, the soap and the water, such as in an amount of 4.25 to 4.75 wt. % based on the total combined amount of the sugar, the fibre, the soap and the water, such as in an amount of 4.3 to 4.7 wt. % based on the total combined amount of the sugar, the fibre, the soap and the water, such as in an amount of 4.4 to 4.6 wt. % based on the total combined amount of the sugar, the fibre, the soap and the water, such as in an amount of approximately 4.5 wt. % based on the total combined amount of the sugar, the fibre, the soap and the water.

The solid cosmetic composition is preferably prepared by dehydrating a liquid composition comprising a vegetable fibre, a fruit fibre or mixture thereof, in an amount of 0.8 to 0.95 wt. % based on the total combined amount of the sugar, the fibre, the soap and the water, such as in an amount of 0.85 to 0.95 wt. % based on the total combined amount of the sugar, the fibre, the soap and the water, such as in an amount of 0.87 to 0.93 wt. % based on the total combined amount of the sugar, the fibre, the soap and the water, such as in an amount of 0.88 to 0.92 wt. % based on the total combined amount of the sugar, the fibre, the soap and the water, such as in an amount of approximately 0.9 wt. % based on the total combined amount of the sugar, the fibre, the soap and the water, such as in an amount 0.8 to 0.9 wt. % based on the total combined amount of the sugar, the fibre, the soap and the water, such as in an amount of 0.82 to 0.88 wt. % based on the total combined amount of the sugar, the fibre, the soap and the water, such as in an amount of approximately 0.85 wt. % based on the total combined amount of the sugar, the fibre, the soap and the water.

The fibre may be obtained from any suitable source. Potential sources include strawberries, mango, pineapple, squashes, potato, sugar beet and mixtures thereof. In one preferred aspect the vegetable fibre, fruit fibre or mixture thereof is obtained from melon. Thus in further aspects the present invention provides

- a solid cosmetic composition comprising (i) sugar; (ii) melon fibre; and (iii) a soap; wherein the solid cosmetic composition is prepared by dehydrating a liquid composition comprising (i) sugar in an amount of 33.75 to 47 wt. %; (ii) melon fibre in an amount of 3.75 to 4.75 wt. %; (iii) a soap in an amount of 20 to 75 wt. %; and (iv) water in an amount of 11 to 15 wt. %, wherein the amounts are based on the total combined amount of the sugar, the fibre, the soap and the water.
- a solid cosmetic composition comprising (i) sugar; (ii) melon fibre; and (iii) a soap; wherein the solid cosmetic composition is prepared by dehydrating a liquid composition comprising (i) sugar in an amount of 6.75 to 8.6 wt. %; (ii) melon fibre in an amount of 0.75 to 0.95 wt. %; (iii) a soap in an amount of 5 to 25 wt. %; and (iv) water in an amount of 67.5 to 85.5 wt. %, wherein the amounts are based on the total combined amount of the sugar, melon fibre, the soap and the water.

The melon which is the source of fibre may be any suitable melon. For example the melon may be of the family *Cucumis*. In one preferred aspect the melon is of the species *Cucumis melo inodorus*. Preferably the melon is honeydew melon.

Although a solid cosmetic product having the required compositional requirements may be prepared from any suitable fruit or vegetable together with sugar and water (as required) we have found that melon provides naturally the desired composition to prepare an effective solid composition for the purposes described herein. Thus in a further aspect the present invention provides a solid cosmetic composition comprising (i) sugar; (ii) melon fibre; and (iii) a soap, wherein the solid cosmetic composition is prepared by dehydrating a liquid composition comprising (a) melon; and (b) a soap.

Typically the (a) melon and (b) soap are combined at a weight ratio of melon to soap of from 19:1 to 3:1, such as from 15:1 to 3:1, such as from 12:1 to 3:1, such as from 10:1 to 3:1, such as from 10:1 to 4:1, such as from 10:1 to 5:1, such as from 10:1 to 6:1, such as from 10:1 to 7:1, such as from 10:1 to 8:1, such as from 10:1 to 9:1, such as from 8:1 to 4:1, such as from 7:1 to 4:1, such as from 6:1 to 4:1, such as from 6:1 to 5:1, such as from 9:1 to 5:1, such as from 7:1 to 5:1, such as from 8:1 to 5:1.

In one aspect (a) honeydew melon and (b) soap are combined at a weight ratio of honeydew melon to soap of from 19:1 to 3:1, such as from 15:1 to 3:1, such as from 12:1 to 3:1, such as from 10:1 to 3:1, such as from 10:1 to 4:1, such as from 10:1 to 5:1, such as from 10:1 to 6:1, such as from 10:1 to 7:1, such as from 10:1 to 8:1, such as from 10:1 to 9:1, such as from 8:1 to 4:1, such as from 7:1 to 4:1, such as from 6:1 to 4:1, such as from 6:1 to 5:1, such as from 9:1 to 5:1, such as from 7:1 to 5:1, such as from 8:1 to 5:1.

Soap

The solid cosmetic product of the present invention comprises a soap.

In the product of the first aspect of the present invention, the solid cosmetic composition comprises a soap in an amount of 20 to 75 wt. % based on the total combined amount of the sugar, the fibre, the soap and the water, such as in an amount of 20 to 60 wt. % based on the total combined amount of the sugar, the fibre, the soap and the water, such as in an amount of 30 to 50 wt % based on the total combined amount of the sugar, the fibre, the soap and the water, such as in an amount of 35 to 45 wt. % based on the total combined amount of the sugar, the fibre, the soap and the water, such as in an amount of 37 to 45 wt. % based on the total combined amount of the sugar, the fibre, the soap and the water, such as in an amount of 39 to 44 wt. % based on the total combined amount of the sugar, the fibre, the soap and the water, such as in an amount of approximately 41.5 wt. % based on the total combined amount of the sugar, the fibre, the soap and the water.

The solid cosmetic composition is preferably prepared by dehydrating a liquid composition comprising a soap in an amount of 5 to 20 wt. % based on the total combined amount of the sugar, the fibre, the soap and the water, such as in an amount of 5 to 15 wt. % based on the total combined amount of the sugar, the fibre, the soap and the water, such as in an amount of 7 to 13 wt. % based on the total combined amount of the sugar, the fibre, the soap and the water, such as in an amount of 8 to 12 wt. % based on the total combined amount of the sugar, the fibre, the soap and the water, such as in an amount of 9 to 11 wt. % based on the total combined amount of the sugar, the fibre, the soap and the water, such as in an amount of approximately 10 wt. % based on the total combined amount of the sugar, the fibre, the soap and the water, such as in an amount of 10 to 20 wt. % based on the total combined amount of the sugar, the fibre, the soap and the water, such as in an amount of 13 to 17 wt. % based on the total combined amount of the sugar, the fibre, the soap and the water, such as in an amount of 14 to 16 wt. % based on the total combined amount of the sugar, the fibre, the soap and the water, such as in an amount of approximately 15 wt. % based on the total combined amount of the sugar, the fibre, the soap and the water.

The soap may be provided in any physical form. Typically the soap is in the form of soap flakes.

The soap of the solid cosmetic composition provides the composition with the ability to achieve its required purpose when used finally. Thus for a body soap, the surfactant removes dirt and grease from the user's skin.

Water

In the product of the first aspect of the present invention, the solid cosmetic composition comprises water in an amount of 11 to 15 wt. % based on the total combined amount of the sugar, the fibre, the soap and the water, such as in an amount of 12 to 15 wt. % based on the total combined amount of the sugar, the fibre, the soap and the water, such as in an amount of 13 to 14 wt. % based on the total combined amount of the sugar, the fibre, the soap and the water, such as in an amount of approximately 13.5 wt. % based on the total combined amount of the sugar, the fibre, the soap and the water.

The solid cosmetic composition is prepared by dehydrating a liquid composition comprising water in an amount of 67.5 to 85.5 wt. % (based on the total combined amount of the sugar, the fibre, the soap and the water). Preferably the solid cosmetic composition is prepared by dehydrating a liquid composition comprising water in an amount of 71.5 to 85.5 wt. % based on the total combined amount of the sugar, the fibre, the soap and the water, such as in an amount of 74 to 85.5 wt. % based on the total combined amount of the sugar, the fibre, the soap and the water, such as in an amount of 77 to 85.5 wt. % based on the total combined amount of the sugar, the fibre, the soap and the water, such as in an amount of 78 to 84 wt. % based on the total combined amount of the sugar, the fibre, the soap and the water, such as in an amount of 79 to 83 wt. % based on the total combined amount of the sugar, the fibre, the soap and the water, such as in an amount of 80 to 82 wt. % based on the total combined amount of the sugar, the fibre, the soap and the water, such as in an amount of approximately 81 wt. % based on the total combined amount of the sugar, the fibre, the soap and the water, such as in an amount of 71.5 to 81.5 wt. % based on the total combined amount of the sugar, the fibre, the soap and the water, such as in an amount of 74 to 79 wt. % based on the total combined amount of the sugar, the fibre, the soap and the water, such as in an amount of approximately 76 wt. % based on the total combined amount of the sugar, the fibre, the soap and the water.

Thickener

In one preferred aspect the solid cosmetic composition further comprises a thickener. Preferably this is selected from cosmetically acceptable clays. Preferably the thickener is selected from kaolin, calamine, smectite clay and mixtures thereof.

It will be appreciated by one skilled in the art that the thickener may be present in any suitable amount to provide the desired solid cosmetic composition. For example the thickener may be present in an amount of 1 to 50 wt. % based on the total weight of the solid composition, such as present in an amount of 2.5 to 25 wt. % based on the total weight of the liquid composition. The solid cosmetic composition may be prepared by dehydrating a liquid composition comprising thickener in an amount of 0.2 to 25 wt. % based on the total weight of the liquid composition, such as in an amount of 0.5 to 5 wt. % based on the total weight of the liquid composition.

Process

As discussed herein, the invention provides a process for preparing a solid cosmetic composition comprising (i) sugar; (ii) a vegetable fibre, a fruit fibre or mixture thereof; and (iii) a soap; the process comprising the step of (a) providing a liquid composition comprising (i) sugar in an amount of 6.75 to 8.6 wt. %; (ii) a vegetable fibre, a fruit fibre or mixture thereof, in an amount of 0.75 to 0.95 wt. %; (iii) a soap in an amount of 5 to 25 wt. %; and (iv) water in an amount of 67.5 to 85.5 wt. %, wherein the amounts are based on the total combined amount of the sugar, the fibre, the soap and the water, (b) dehydrating the liquid composition to provide the solid cosmetic composition.

Preferably the liquid composition is provided by mixing
(a) melon; and
(b) a soap.

Thus in one aspect the present invention provides a process for preparing a solid cosmetic composition comprising (i) sugar; (ii) melon fibre; and (iii) a soap; the process comprising the steps of
(a) providing a liquid composition comprising (i) melon; and (ii) soap,
(b) dehydrating the liquid composition to provide the solid cosmetic composition.

In a further aspect the present invention provides a process for preparing a solid cosmetic composition comprising (i) sugar; (ii) honeydew melon fibre; and (iii) a soap; the process comprising the steps of
(a) providing a liquid composition comprising (i) honeydew melon; and (ii) soap,
(b) dehydrating the liquid composition to provide the solid cosmetic composition.

The shape of the solid products of the present invention is not limited. However, they are typically dehydrated in the form of a sheet. However, it is envisaged that they may be produced in the form from which sheets may be cut or sliced.

As described herein, the solid product may further comprise one or more cosmetically acceptable additives. In one embodiment, the process further comprises the step of combining with the liquid composition, one or more cosmetically acceptable additives as defined herein.

The liquid composition is dehydrated to provide the solid cosmetic composition using any suitable dehydrating technique. In a typical technique the liquid composition is poured on to a flat sheet. Preferably the flat sheet is made of silicone to help prevent the dehydrated product from sticking to the flat sheet. Preferably the liquid is poured to a depth of half a centimeter thick. The liquid product may then be placed in a de-hydrating oven, for example at a temperature of 55° C. for between 8 to 15 hours. This time and temperature may be varied depending on the liquid composition.

The present invention also provides a product obtained or obtainable by a process described herein.

Additional Components

The solid product of the present invention may also comprise one or more cosmetically acceptable additives. The person skilled in the art is aware of a range of cosmetically acceptable additives which are suitable for incorporation into such compositions. For example, binders, fillers, opacifiers, perfumes, colours, fragrances, decorative items, herbs and mixtures thereof. Preferably the solid cosmetic composition comprises at least one additional component selected from colours, fragrances, herbs and mixtures thereof.

The combined amount of cosmetically acceptable additives is preferably from about 0.1% to about 20% by weight of the total solid composition, such as from about 0.1% to about 10% by weight of the total solid composition, such as from about 1% to about 10% by weight of the total solid composition, such as from about 2% to about 10% by weight of the total solid composition, such as from about 4% to about 10% by weight of the total solid composition, such as from about 4% to about 8% by weight of the total solid composition, such as from about 5% to about 7% by weight of the total solid composition.

The combined amount of colours and fragrances is preferably from about 0.1% to about 10% by weight of the total solid composition, such as from about 0.1% to about 5% by weight of the total solid composition, such as from about 0.5% to about 5% by weight of the total solid composition, such as from about 1% to about 5% by weight of the total solid composition, such as from about 1% to about 4% by weight of the total solid composition, such as from about 1% to about 3% by weight of the total solid composition, such as from about 1% to about 2% by weight of the total solid composition.

Fruit and herb extracts and juices, vegetable oils and essential oils are all compatible with the solid composition. Colours, both naturally derived and synthetic can be used to colour the product. Cosmetic colour is added to the invention to form bright colourful shapes and bars of the mixture. This colour can be a blend of synthetic cosmetic pigments, such as FD&C Blue No1, FD&C Red No 4 and others. Also naturally derived colours such as gardenia extract or chloropyl extract.

The amount of colour is preferably from about 0.01% to about 10% by weight of the total solid composition, such as from about 0.01% to about 5% by weight of the total solid composition, such as from about 0.01% to about 4% by weight of the total solid composition, such as from about 0.01% to about 3% by weight of the total solid composition, such as from about 0.01% to about 2% by weight of the total solid composition, such as from about 0.02% to about 2% by weight of the total solid composition, such as from about 0.05% to about 2% by weight of the total solid composition, such as from about 0.1% to about 2% by weight of the total solid composition, such as from about 0.2% to about 2% by weight of the total solid composition, such as from about 0.2% to about 1% by weight of the total solid composition, such as from about 0.2% to about 0.8% by weight of the total solid composition, such as from about 0.2% to about 0.6% by weight of the total solid composition, such as from about 0.4% to about 0.6% by weight of the total solid composition.

In one embodiment, the cosmetically acceptable additives are selected from the group consisting of essential oils, vitamins, fragrances, colourings, clays, decorative articles, herbs and mixtures thereof.

The amount of herbs is preferably from about 0.1% to about 10% by weight of the total solid composition, such as from about 1% to about 10% by weight of the total solid composition, such as from about 1% to about 8% by weight of the total solid composition, such as from about 2% to about 8% by weight of the total solid composition, such as from about 3% to about 7% by weight of the total solid composition, such as from about 4% to about 6% by weight of the total solid composition.

Fragrance may be added to the product to make the experience of using the present composition more pleasant. combining essential oils such as lavender, chamomile or rose absolute into fragrances for the invention ensures the user has a pleasant washing experience.

The amount of fragrances is preferably from about 0.1% to about 10% by weight of the total solid composition, such as from about 0.1% to about 5% by weight of the total solid composition, such as from about 0.1% to about 4% by weight of the total solid composition, such as from about 0.5% to about 5% by weight of the total solid composition, such as from about 1% to about 5% by weight of the total solid composition, such as from about 0.5% to about 4% by weight of the total solid composition, such as from about 0.5% to about 3% by weight of the total solid composition, such as from about 0.5% to about 2% by weight of the total solid composition, such as from about 0.5% to about 1.5% by weight of the total solid composition.

The essential oils may be selected based on the fragrance desired, skin type to be treated and other effects desired based on the well known properties of essential oils. The addition of essential oils, when taken in to the nose, are known to alter mood. For example, essential oils are known to create effects of drowsiness or stimulating the senses. Many well documented effects can be achieved by the use of essential oils.

In one embodiment, the one or more essential oils present in the solid product are selected from Tarragon, Lemon myrtle, Jasmin, Ylang ylang, Labdanum, Lemongrass, Rose otto, Grapefruit, Patchouli, Rosemary, Armois, Lemon, Neroli, Sweet violet, Lavender, Orange 50 fold, Vanilla, Peppermint, Benzoin, Hydrangia, Litsea Cubeba, Cardamon, Tonka, and Chamomile blue. In one embodiment, the one or more essential oils present in the solid product are selected from Tarragon, Lemon myrtle, Labdunum, and Lemon.

Vitamins, particularly B, C and E are very beneficial for the skin. Vitamin rich ingredients such as Wheatgerm oil can also be used to deliver vitamins on to the skin. In a one embodiment, the vitamins are selected from vitamin B, vitamin C, vitamin E and mixtures thereof. It will be appreciated by one skilled in the art that the vitamin may be provided from any suitable source. For example the vitamin(s) may be provided from a synthetic source or from incorporation into the solid product of a material, such as a natural material, that has a high vitamin content.

The ingredients of the present invention do not require cosmetic preservatives. The use of cosmetic preservatives can increase the potential to irritate the skin.

The above ranges provide preferred amounts of each of the components. Each of these ranges may be taken alone or combined with one or more other component ranges to provide a preferred aspect of the invention.

Method

In one aspect of the present invention, there is provided a method comprising contacting the skin of a user with water in which the solid product as defined herein has dissolved or in which the solid product as defined herein is dissolving.

EXAMPLES

The invention will now be described with reference to the following non-limiting example.

A solid product having the following composition was prepared.

On exploring the functionality of fruits and vegetables it was found that melon and in particular the variety of melon known as Honeydew was the most effective when blended with soap to make the paper. The form of soap most useful in the blend is soapflakes. The proportion of melon to soapflakes prepared is as follows:

| Soapflakes | 15 wt. % |
|---|---|
| Honeydew Melon | 85 wt. % |

The method of manufacture of the invention is as follows;
1. Remove the flesh from the melon. Make a puree of this blending to a runny pulp-like texture.
2. Grind the soapflakes to a fine powder.
3. Add the powdered soapflakes to the melon and leave to stand for fifteen to twenty minutes.
4. Pour on to a silicone flat sheet. Pour to a depth of half a centimeter thick.
5. Place the sheet in to a de-hydrating oven at a temperature of 55° C. for between 8 to 15 hours, the time depending on the blend.
6. When dry, remove carefully from the sheet.

The dehydration of the mixture evaporates the major part of the water content. This leaves the fruit fibres and the soapflakes to form structure. The solid composition is approximately one sixth of the weight of the liquid composition from which it is prepared.

Example 1

In one embodiment a composition is prepared containing water, sugar, fibre and soapflakes in the following proportions by weight:

| | |
|---|---|
| Water | 76.5% |
| Sugar (raw cane sugar) | 7.65% |
| Fruit Fibre | 0.85% |
| Soap | 15% |
| TOTAL | 100% |

The product was dehydrated to provide a sheet of soap product that was pliable and foldable.

Example 2

In a further embodiment a composition is prepared containing water, sugar, fibre, soapflakes and clay in the following proportions by weight:

| | |
|---|---|
| Smectite Clay | 0.5% |
| Water | 76% |
| Sugar (raw cane sugar) | 7.65% |
| Fibre | 0.85% |
| Soap | 15% |
| TOTAL | 100% |

The product was dehydrated to provide a sheet of soap product that was pliable and foldable.

Example 3

In a further embodiment a composition is prepared containing water, sugar, fibre and soapflakes in the following proportions by weight:

| | | |
|---|---|---|
| Water | 81 g | 81% |
| Sugar (raw cane sugar) | 8.1 g | 8.1% |
| Fruit Fibre | 0.9 g | 0.9% |
| Soap | 10 g | 10% |
| TOTAL | 100 g | 100% |

The composition was subjected to dehydration and the water lost during dehydration was recorded by measuring the mass of the product before and after dehydration. Based on the known loss of water, the composition of the product after dehydration was determined to be

| | |
|---|---|
| Water | 13.5% |
| Sugar (raw cane sugar) | 40.5% |
| Fruit Fibre | 4.5% |
| Soap | 41.5% |
| TOTAL | 100% |

The dehydrated product was a sheet of soap product that was pliable and foldable.

The fibres of these three two examples are from honeydew melon. Alternatively they may be from strawberries, mango, pineapple, squashes, potato, sugar beet and mixtures thereof.

Products prepared in accordance with the present invention are pliable and foldable. They are used to wrap other cosmetics. Boxes of cosmetics are wrapped with defined folds being created in the sheet of solid product without cracking of the product. The wrapped box can also be unwrapped without breaking of the sheet of solid product.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A solid cosmetic composition comprising:
    (i) sugar;
    (ii) melon fiber; and
    (iii) a soap;
    wherein the solid cosmetic composition is prepared by dehydrating a liquid composition comprising:
        (i) sugar in an amount of 6.75 to 8.6 wt. %;
        (ii) melon fiber in an amount of 0.75 to 0.95 wt. %;
        (iii) soap in an amount of 5 to 25 wt. %; and
        (iv) water in an amount of 67.5 to 85.5 wt. %,
        wherein the amounts are based on the total combined amount of the sugar, the melon fiber, the soap and the water in the liquid composition.

2. A solid cosmetic composition according to claim 1, wherein the solid cosmetic composition comprises:
    (i) sugar in an amount of 33.75 to 47 wt. % based on the total combined amount of the sugar, the melon fiber, the soap and the water.

3. A solid cosmetic composition according to claim 1, wherein the solid cosmetic composition comprises
    (i) sugar in an amount of 38 to 45 wt. % based on the total combined amount of the sugar, the melon fiber, the soap and the water.

4. A solid cosmetic composition according to claim 1, wherein the solid cosmetic composition comprises
    (ii) melon fiber in an amount of 3.75 to 4.75 wt. % based on the total combined amount of the sugar, the melon fiber, the soap and the water.

5. A solid cosmetic composition according to claim 1, wherein the solid cosmetic comprises
    (ii) melon fiber in an amount of 4.25 to 4.75 wt. % based on the total combined amount of the sugar, the melon fiber, the soap and the water.

6. A solid cosmetic composition according to any one of the preceding claims, wherein the solid cosmetic composition comprises
    (iii) a soap in an amount of 20 to 75 wt. % based on the total combined amount of the sugar, the melon fiber, the soap and the water.

7. A solid cosmetic composition according to claim 1, wherein the solid cosmetic composition comprises
    (iii) a soap in an amount of 30 to 50 wt. % based on the total combined amount of the sugar, the melon fiber, the soap and the water.

8. A solid cosmetic composition according to any one of the preceding claims, wherein the solid cosmetic composition comprises:
    (iv) water in an amount of 11 to 15 wt. % based on the total combined amount of the sugar, the melon fiber, the soap and the water.

9. A solid cosmetic composition according to claim 1, wherein the solid cosmetic composition comprises
    (iv) water in an amount of 13 to 14 wt. % based on the total combined amount of the sugar, the melon fiber, the soap and the water.

10. A solid cosmetic composition according to claim 1, wherein the sugar is sucrose.

11. A solid cosmetic composition according to claim wherein the melon is honeydew melon.

12. A solid cosmetic composition according to claim 1, wherein the soap is in the form of soap flakes.

13. A solid cosmetic composition according to claim 1, wherein the solid cosmetic composition further comprises a thickener.

14. A solid cosmetic composition according to claim 13, wherein the thickener is selected from cosmetically acceptable clays.

15. A solid cosmetic composition according to claim 13, wherein the thickener is present in an amount of 1 to 50 wt. % based on the total weight of the solid composition.

16. A solid cosmetic composition according to claim 13, wherein the thickener is present in an amount of 2.5 to 25 wt. % based on the total weight of the solid composition.

17. A solid cosmetic composition according to claim 1, further comprising at least one additional component selected from binders, fillers, opacifiers, perfumes, colours, fragrances, decorative items, herbs and mixtures thereof.

18. A solid cosmetic composition according to claim 17, further comprising at least one additional component selected from colours, fragrances, herbs and mixtures thereof.

19. A solid cosmetic composition according to claim 18, wherein the combined amount of colours and fragrances is from 0.1 to 30 wt. % based on the total weight of the solid composition.

20. A solid cosmetic composition according to claim 18, comprising herbs in an amount of 5 to 50 wt. % based on the total weight of the solid composition.

21. A solid cosmetic composition comprising
    (i) sugar;
    (ii) melon fiber; and
    (iii) a soap,
    wherein the solid cosmetic composition is prepared by dehydrating a liquid composition comprising
        (a) melon fiber; and
        (b) a soap.

22. A solid cosmetic composition according to claim 21, wherein the weight ratio of melon to soap is from 19:1 to 3:1.

23. A solid cosmetic composition according to claim 21, wherein the weight ratio of melon to soap is from 7:1 to 5:1.

24. A process for preparing a solid cosmetic composition comprising
    (i) sugar;
    (ii) melon fiber; and
    (iii) a soap;

the process comprising the step of:
(a) providing a liquid composition comprising:
 (i) sugar in an amount of 6.75 to 8.6 wt. %;
 (ii) melon fiber in an amount of 0.75 to 0.95 wt. %;
 (iii) a soap in an amount of 5 to 25 wt. %; and
 (iv) water in an amount of 67.5 to 85.5 wt. %,
 wherein the amounts are based on the total combined amount of the sugar, the melon fiber, the soap and the water in the liquid composition,
(b) dehydrating the liquid composition to provide the solid cosmetic composition.

* * * * *